United States Patent
DeBusk et al.

(10) Patent No.: US 12,100,029 B2
(45) Date of Patent: Sep. 24, 2024

(54) AUTOMATED SYSTEM FOR MEDICAL ITEM DISPENSING, BILLING, AND INVENTORY MANAGEMENT

(71) Applicant: DeRoyal Industries, Inc., Powell, TN (US)

(72) Inventors: Brian C. DeBusk, Knoxville, TN (US); Angela M. Sewell, Knoxville, TN (US); John G. Jacobs, Knoxville, TN (US); Gregory S. Hodge, Knoxville, TN (US); Kevin E. Lynch, Knoxville, TN (US); William G. Pittman, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 588 days.

(21) Appl. No.: 17/313,098

(22) Filed: May 6, 2021

(65) Prior Publication Data
US 2021/0272169 A1    Sep. 2, 2021

Related U.S. Application Data

(60) Division of application No. 14/978,156, filed on Dec. 22, 2015, now abandoned, which is a
(Continued)

(51) Int. Cl.
G06Q 30/04       (2012.01)
G06Q 10/087      (2023.01)
(Continued)

(52) U.S. Cl.
CPC .......... *G06Q 30/04* (2013.01); *G06Q 10/087* (2013.01); *G06Q 10/10* (2013.01); *G06Q 20/102* (2013.01);
(Continued)

(58) Field of Classification Search
None
See application file for complete search history.

(56) References Cited

U.S. PATENT DOCUMENTS

| 2004/0046020 A1* | 3/2004 | Andreasson | A61J 1/14 235/385 |
| 2005/0110638 A1* | 5/2005 | Mohr | B25H 3/00 340/568.1 |

(Continued)

FOREIGN PATENT DOCUMENTS

AU   2003259259 A1 *  2/2004  ............ A61J 7/0084

OTHER PUBLICATIONS

Dubourg, Gladys. "Establishing an Outsourcing Program Needed for the Packaging and Labeling of Pharmaceutical Products used during Clinical Trials for XYZ Corporation." Order No. 1417407 California State University, Dominguez Hills, 2003. Ann Arbor: ProQuest. Web. Jul. 3, 2024. (Year: 2003).*

(Continued)

*Primary Examiner* — Lena Najarian
(74) *Attorney, Agent, or Firm* — Luedeka Neely, P.C.

(57) ABSTRACT

An inventory management system manages information regarding medical items dispensed to a patient in a medical facility. Inventory sensors sense removal of medical items from an inventory space to be dispensed to the patient. Software instructions associate item information with patient information that identifies the patient, determine billing codes associated with the dispensed items, generate billing information including the patient information and the billing codes, and generate an invoice directed to the patient's medical insurance provider. The instructions also verify that the billing codes are associated with medical items appropriate for treatment of the patient's condition indicated by diagnostic codes included in the billing information, and generate an alert message if the billing codes are (Continued)

associated with medical items that are not reimbursable or are inappropriate for treatment of the diagnosed condition. The alert message is sent to the physician who diagnosed the patient and provided the diagnostic code.

15 Claims, 8 Drawing Sheets

Related U.S. Application Data continuation-in-part of application No. 13/546,324, filed on Jul. 11, 2012, now Pat. No. 9,990,466, and a continuation-in-part of application No. 13/448,732, filed on Apr. 17, 2012, now abandoned, and a continuation-in-part of application No. 13/223,641, filed on Sep. 1, 2011, now Pat. No. 8,818,824.

(51) Int. Cl.
*G06Q 10/10* (2023.01)
*G06Q 20/10* (2012.01)
*G07F 17/00* (2006.01)
*G16H 10/60* (2018.01)
*G16H 10/65* (2018.01)
*G16H 20/13* (2018.01)
*G16H 40/20* (2018.01)

(52) U.S. Cl.
CPC ......... *G07F 17/0092* (2013.01); *G16H 10/60* (2018.01); *G16H 10/65* (2018.01); *G16H 20/13* (2018.01); *G16H 40/20* (2018.01)

(56) References Cited

U.S. PATENT DOCUMENTS

| | | | | |
|---|---|---|---|---|
| 2006/0006999 | A1* | 1/2006 | Walczyk | G06Q 10/08 340/572.1 |
| 2006/0229551 | A1* | 10/2006 | Martinez | G16H 20/17 604/67 |
| 2007/0208598 | A1* | 9/2007 | McGrady | G16H 15/00 705/3 |
| 2008/0100455 | A1* | 5/2008 | Erickson | G06K 19/07749 340/572.8 |
| 2008/0195247 | A1* | 8/2008 | Mallett | G07F 11/62 700/231 |
| 2008/0316045 | A1* | 12/2008 | Sriharto | G16H 20/13 700/214 |
| 2010/0036755 | A1* | 2/2010 | Saghbini | G06Q 10/00 705/28 |
| 2010/0141457 | A1 | 6/2010 | Wass et al. | |
| 2011/0139871 | A1* | 6/2011 | Yturralde | G06K 7/10336 235/492 |
| 2012/0203566 | A1* | 8/2012 | Kidd | G16H 40/40 705/2 |
| 2014/0048593 | A1 | 2/2014 | Hoganson | |

OTHER PUBLICATIONS

Anna-Marie Vilamovska, Improving the quality and cost of health care delivery; The potential of radio frequency identification (RFID) technology; The Pardee RAND Graduate School ProQuest Dissertations Publishing, 2010 (Year: 2010).

\* cited by examiner

AUTOMATED SYSTEM FOR MEDICAL ITEM DISPENSING, BILLING, AND INVENTORY MANAGEMENT

This application is a divisional of and claims priority to co-pending U.S. patent application Ser. No. 14/978,156 filed Dec. 22, 2015, which is a continuation-in-part of and claims priority to co-pending U.S. patent application Ser. No. 13/546,324 filed Jul. 11, 2012, which is a continuation-in-part of U.S. patent application Ser. No. 13/223,641 filed Sep. 1, 2011, which issued as U.S. Pat. No. 8,818,824, and which is a continuation-in-part of co-pending U.S. patent application Ser. No. 13/448,732 filed Apr. 17, 2012. All of these applications are titled AUTOMATED SYSTEM FOR MEDICAL ITEM DISPENSING, BILLING, AND INVENTORY MANAGEMENT.

FIELD

This invention relates to an inventory management system. More particularly, this invention relates to a system for managing inventories of medical supply items.

BACKGROUND OF THE INVENTION

Durable Medical Equipment (DME), Prosthetics, Orthotics and Supplies (DMEPOS) as defined by the Department of Health and Human Services and its Center for Medicare Services (CMS) is a class of medical devices, products and supplies that are typically reimbursable under Part B of the U.S. Medicare health care program. In general, this category of products includes items provided to patients who receive outpatient treatment for certain health problems that do not require inpatient admission to a hospital or other healthcare institution. DMEPOS items are typically provided or prescribed to help alleviate, treat or assist in recovery from the condition that prompted the outpatient treatment of the patient. Such outpatient treatment can occur in any number of settings, such as a hospital emergency department, a clinic, or a physician's or therapist's office.

In general, the costs of DMEPOS items are reimbursable or payable separately from the healthcare professional's fee for treatment of the patient. DMEPOS items are typically reimbursable or payable in both Medicare and Medicaid programs and through private health insurers. Traditionally, most DMEPOS items were prescribed by the treating professional and those prescriptions could be filled by DME shops, Orthotics/Prosthetics shops, pharmacies with DME services, etc. However, as a convenience to patients many healthcare providers would like to dispense DMEPOS items at the time of treatment of the patient in order to facilitate patient convenience and continuity of care.

Since DMEPOS items are typically reimbursable or payable under a different billing and reimbursement system than professional healthcare services, it has been difficult for healthcare professionals to provide the dispensing of these items as an adjunct service to their patients. The specialty shops that have traditionally dispensed these items have developed the business processes necessary to properly stock the products, manage the inventory, properly associate prescriptions for DMEPOS items with appropriate coding under the CMS coding system, generate the regulatory paperwork for delivery of the item to the patient and generate the necessary forms for submission to the reimbursement agency such as Medicare, Medicaid, or private insurance.

Healthcare providers have a need to dispense DMEPOS items as an adjunct service to their medical practice, without having to individually develop all of the business processes which suppliers have developed previously and without the labor and overhead costs associated with those types of suppliers. Healthcare providers need to be able to supply the patient with DMEPOS products that the healthcare provider has evaluated and knows to be appropriate for the patient's particular diagnosis and indications. It would be a significant advantage for the patient if the healthcare provider could provide the DMEPOS item at the time of initial diagnosis and treatment of the patient. This would allow the healthcare provider to properly fit the item to the patient and instruct the patient on the proper use of the item. For the patient, this would minimize the hassle of having to go to other locations to complete the diagnosis and treatment, and would generally result in better continuity of care.

SUMMARY OF THE INVENTION

The above and other needs are met by an inventory management system for managing information regarding medical items dispensed in conjunction with medical treatment of patients in a medical facility, wherein each medical item has an associated billing code. In a preferred embodiment, the system includes inventory sensors that sense removal of medical items from an inventory space to be dispensed for treatment of a patient and that generate item usage information indicative of an identity and quantity of the medical items removed. The inventory sensors may include a weight sensor attached to a storage structure in the inventory space, an RFID sensor for sensing the presence of an RFID tag attached to a medical item in the inventory space, a bar code reader for scanning a barcode on a medical item, a digital camera for capturing an image of a medical item, or a combination of these sensors. The system also includes one or more computers that are configured to store and process item usage information and billing information for medical items dispensed to patients, wherein the billing information includes billing codes for medical items.

One or more software applications, which are executed on one or more of the computers, include instructions that are automatically executed based on the removal of the medical items as sensed by the inventory sensors. The computer-executable instructions (1) associate the item usage information with patient information that identifies the patient to which the medical items are dispensed, (2) determine billing codes that are associated with the medical items dispensed to the patient and associate billing codes with the item usage information, (3) generate billing information that includes the item usage information, the patient information, and the billing codes associated with the medical items dispensed to the patient, and (4) generate an invoice directed to the patient's medical insurance provider based on the billing information.

In some embodiments, the computer-executable instructions generate billing information that includes a diagnostic code indicative of a diagnosis of the patient to which the medical items were dispensed. The instructions verify that the billing codes included in the billing information are associated with medical items that are appropriate for treatment of the diagnosed injury or condition indicated by the diagnostic code included in the billing information. The instructions automatically generate an alert message when it is determined that the billing codes included in the billing information are associated with medical items that are not reimbursable or are inappropriate for treatment of the diagnosed injury or condition indicated by the diagnostic code included in the billing information. The instructions communicate the alert message to the computer of a physician who diagnosed the patient and provided the diagnostic code.

Some embodiments provide an inventory management system for managing information regarding medical items dispensed in conjunction with medical treatment of a patient, which medical items are disposed in storage containers in a storage structure. The inventory management system includes a physician interface device that is operable to communicate via a communication network. A treatment protocol application, which runs on or is in communication with the physician interface device, includes computer-executable instructions that (1) access a listing of medical items from which the physician may select to be dispensed for treating a diagnosed medical condition of the patient, (2) generate item dispensing information including first patient information that identifies the patient to whom the selected medical items are to be dispensed, and (3) communicate the item dispensing information via the communication network. The system also includes a customer computer that is in communication with the physician interface device via the communication network.

RFID sensors are disposed in the storage structure which are in communication with the customer computer. The RFID sensors are operable to sense second patent information that is encoded in a patient identifier RFID tag that enters the storage structure. One or more display devices are also disposed in the storage structure and are in communication with the customer computer. One or more software applications, which run on or are in communication with the customer computer, include computer-executable instructions that (1) receive the item dispensing information from the communication network, (2) process the item dispensing information to determine which medical items are to be removed from the storage containers to be dispensed to the patient, (3) process the first patent identification information included in the item dispensing information to identify the patient to whom the medical items are to be dispensed, (4) process the second patient information encoded in the patient identifier RFID tag to determine whether the second patient information identifies the same patient as the first patient information, and (5) if the second patient information matches the first patient information, activate the one or more of the display devices in the storage structure to visually indicate which storage containers contain medical items that are to be dispensed to the patient identified by the first and second patient information.

In some embodiments, the RFID sensors sense the second patent information encoded in the patient identifier RFID tag attached to the patient's chart or other documentation that enters the storage structure.

In some embodiments, the display devices comprise multiple lights disposed in the storage structure. Each light is associated with a corresponding one of the storage containers and provides a visual indication that one or more medical items are to be removed from the storage container associated with the light. In some embodiments, a display screen displays information listing the one or more medical items that are to be removed from the storage containers to be dispensed to the patient identified by the first and second patient information.

In another aspect, the invention provides an inventory management system for managing information regarding medical items listed on a discharge order to be dispensed in conjunction with medical treatment of a patient. The medical items are disposed in storage containers in a discharge closet. In a preferred embodiment, the inventory management system includes one or more RFID sensors disposed in the discharge closet that sense patient identification information encoded in an RFID tag attached to the discharge order when the discharge order enters the discharge closet. The system includes one or more display devices disposed in the discharge closet, and one or more computers that are in communication with the RFID sensors and the display devices.

The one or more computers are configured to store and process billing information for medical items dispensed to patients. The billing information includes information that associates each patient with a medical insurance provider to which medical expenses incurred by the patent are to be billed. The billing information also includes information that associates medical items stored in the discharge closet with medical insurance providers that provide reimbursement for the associated medical items.

The system includes software applications that are executed on the one or more computers. The software applications include instructions that (1) process the patient identification information to identify a patient associated with the discharge order, (2) process the billing information to identify a medical insurance provider to which medical expenses incurred by the patient associated with the discharge order are to be billed, (3) process the billing information to identify medical items stored in the discharge closet for which reimbursement is provided by the identified medical insurance provider, and (4) activate the display devices in the discharge closet to visually indicate storage containers in which the identified medical items are disposed.

In some embodiments, the one or more computers automatically execute the instructions based on the RFID sensors sensing patient identification information encoded in the RFID tag attached to the discharge order when the discharge order enters the discharge closet.

In some embodiments, the system includes inventory sensors for sensing removal of medical items from the storage containers. The inventory sensors may include a weight sensor attached to the storage container from which the medical item was removed, an RFID sensor for sensing the presence of an RFID tag attached to the removed medical item, a bar code reader for scanning a barcode on the removed medical item, a digital camera for capturing an image of the removed medical item, or a combination of these sensors. The software applications include computer-executable instructions that (1) identify the removed medical item based on a signal from a weight sensor attached to the storage container from which the medical item was removed, or based on information contained in an RFID tag attached to the removed medical item, or based on information contained in a barcode on the removed medical item, or based on an image of the removed medical item, (2) determine whether the removed medical item is a medical item for which reimbursement is provided by the identified medical insurance provider, and (3) generate an alarm if the removed medical item is not a medical item for which reimbursement is provided by the identified medical insurance provider.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION OF EMBODIMENTS OF THE INVENTION

Figure 4:
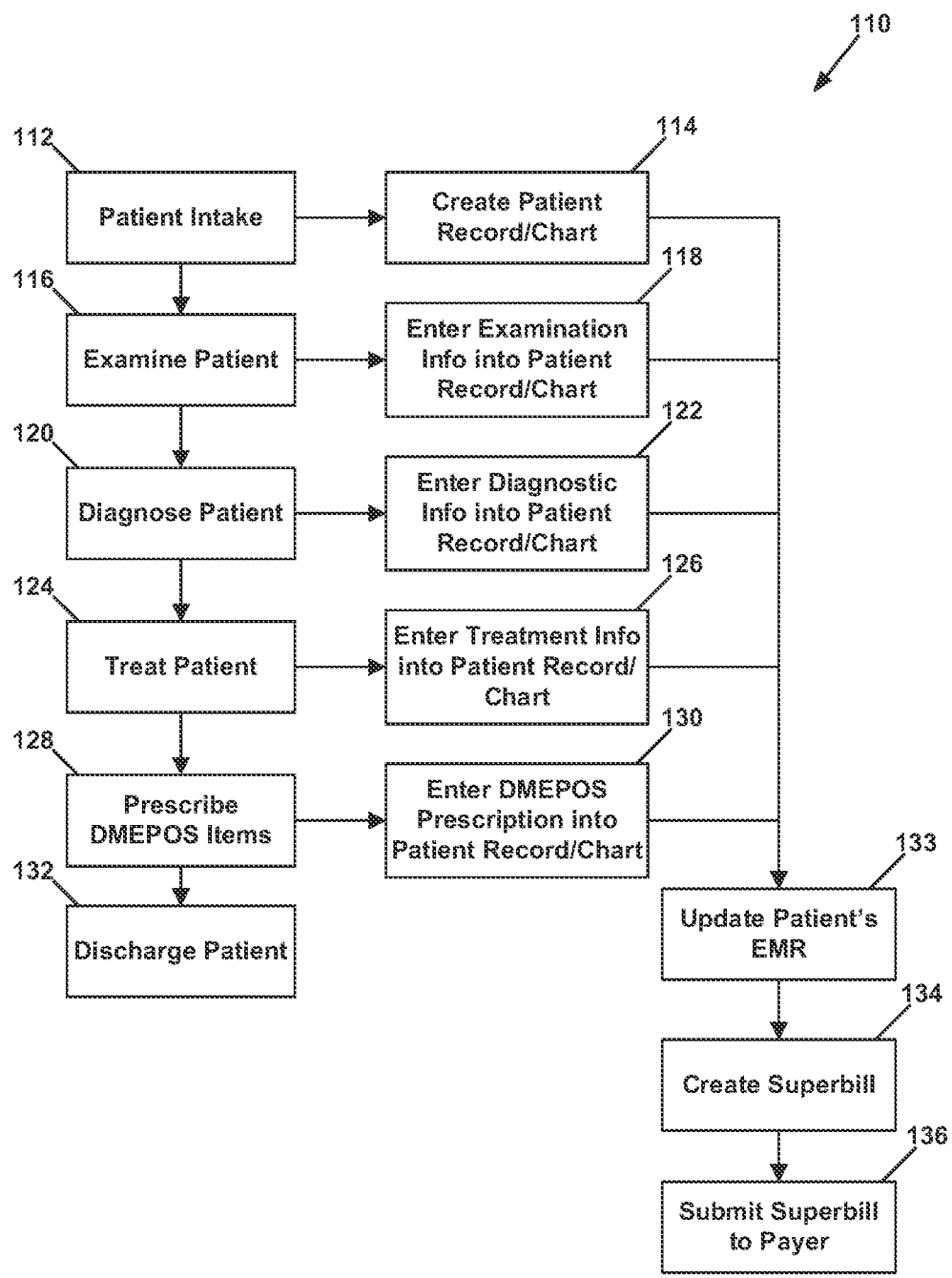
FIG. 4 depicts a typical workflow for the provision of DMEPOS items based on traditional practices.

A typical workflow for the provision of DMEPOS items under traditional practices is depicted in FIG. 4. Generally, a patient follows a treatment path 110 that typically begins with the patient arriving at a treatment facility with a medical condition and ends with the patient being discharged or leaving the treatment facility. Examples of treatment facilities include a hospital emergency department, a physician's office, a clinic, and a therapy office. The first step in the treatment path 110 is typically patient intake (step 112) in which information concerning the patient is recorded and a patient record/chart (or face sheet) is created as an output (step 114). Typically, patient intake (step 112) includes collecting of basic demographic and medical information about the patient, as well as payment responsibility information, such as insurance information (either private insurance or information regarding participation in a government program such as Medicare/Medicaid). This information is recorded in the patient record/chart, which is typically created in electronic form in a pre-existing information system resident in the treatment facility.

Following patient intake (step 112) is the examination of the patient (step 116). In this step, the appropriate healthcare provider examines the patient, takes a patient history, and reviews the symptoms. The examination (step 116) may also include other diagnostic activities such as lab work and imaging that assist the provider in making an accurate diagnosis. Examination information is typically recorded into the patient record/chart (step 118). The healthcare provider then makes a diagnosis of the patient (step 120), and the diagnostic information, such as diagnostic codes, are also entered into the patient record/chart (step 122).

After diagnosis (step 120) and entering the diagnostic information in the patient record/chart (step 122), the next step is typically treatment of the patient (step 124). In the context of this invention, treatment of the patient typically includes the healthcare provider prescribing or providing a DMEPOS item, such as an orthotic, to facilitate treatment of the diagnosed condition (step 128). Information regarding the treatment, including DMEPOS prescription information, is entered into the patient record/chart (steps 126 and 130), and this information is entered in the patient's Electronic Medical Records (step 133).

The final step in the treatment path 110, is for the patient to be discharged or released (step 132). The information entered into the patient record/chart at each step in the treatment path 110 is used to supply information to create a Medicare-complaint bill reflecting all of the billable services provided in the process (step 134). This information is then uploaded to the appropriate billing software for submittal to a payer (step 136).

Figure 1:
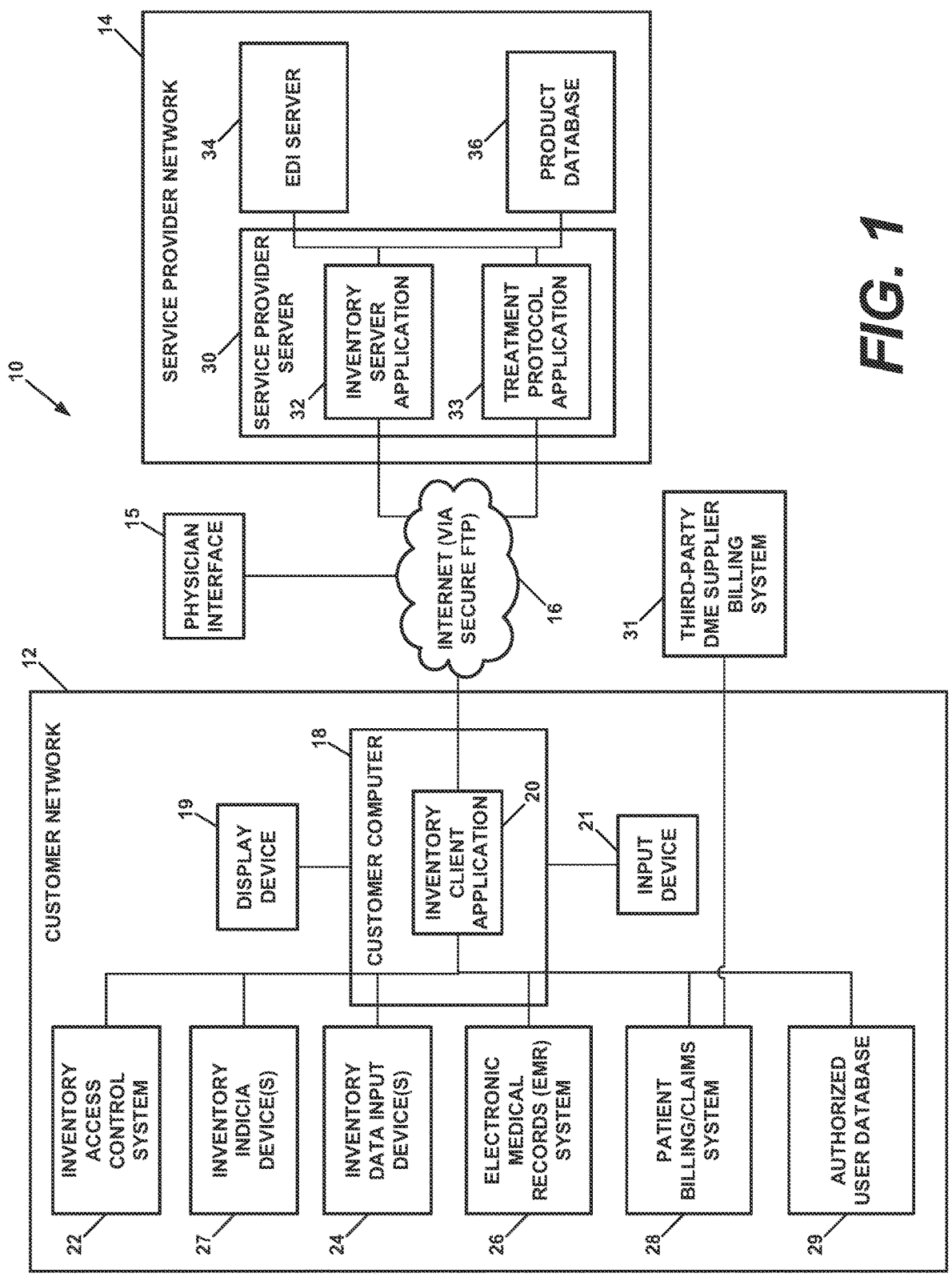
FIG. 1 is a functional block diagram of an embodiment of a medical product/supply dispensing, billing and inventory management system.

FIG. 1 depicts an embodiment of a medical product/supply dispensing, billing and inventory management system 10. As described in more detail hereinafter, the system 10 provides computer-implemented tools and processes for managing an inventory of medical products/supplies, for dispensing such products/supplies to patients, and for billing a payer for the dispensed products/supplies. However, one skilled in the art will recognize that the system 10 may be used to manage inventories of other components and materials in medical and nonmedical applications. Thus, the embodiments described herein are not limited only to medical product/supply inventory, dispensing, and billing applications.

As shown in FIG. 1, the system 10 includes a customer computer network 12 and a service provider computer network 14 that communicate with each other via a communication network 16 such as the Internet. As the term is used herein, "customer" generally refers to a medical facility where medical diagnostic and treatment procedures are performed, such as a hospital, outpatient surgical center, physician's office, clinic, or therapy office. The term "customer" may also refer to any consumer of products/supplies that are inventoried and managed using the system described herein. Accordingly, one or more of the components of the customer computer network 12 may be located within a hospital, clinic, doctor's office, or other medical facility.

The customer computer network 12 includes a customer computer 18 that is operable to communicate through the Internet 16 with the service provider computer network 14. The customer computer 18 may be, for example, a desktop computer, laptop computer, tablet computer, or smart phone. In preferred embodiments, an inventory client application 20 is loaded on the customer computer 18 to provide some or all of the inventory management, dispensing, and billing functions described herein. The customer computer 18 and the client application 20 are in communication with an inventory access control system 22, one or more inventory sensors 24, an Electronic Medical Records (EMR) computer system 26, and a patient billing/claims computer system 28. A user input device 21, such as a keyboard or mouse or touchpad, is preferably provided as a component of the customer computer 18. In a preferred embodiment, the customer computer 18 also includes a display device 19 within the inventory space on which the inventory client application 20 displays information regarding inventory transactions. In some embodiments, the display device 19 and user input device 21 are combined as a touch screen device.

The inventory access control system 22 comprises a keypad, magnetic stripe reader (card swipe), proximity reader, RFID tag reader, biometric sensor device, a digital camera and facial recognition software, or other entry-access device that authorized customer personnel use to gain access to a medical product/supply inventory space. The inventory space may be a secured, limited-access location in the customer facility in which DMEPOS items are stored. In preferred embodiments, the inventory access control system 22 communicates with the customer computer 18 via a wired or wireless network connection.

As the term is used herein, an "inventory space" may be a secured, limited access inventory room or supply room. Alternatively, an inventory space may be a storage structure, such as cabinet, box, cage or other enclosure. In some embodiments, multiple inventory spaces may be provided in a single room. For example, there may be one secured cabinet containing DMEPOS items and another secured cabinet in the same supply room containing surgical implant items. In some embodiments, the inventory space may be an unsecured space into which anyone may enter or gain access.

As the term is used herein, a "storage container" may be a bin, drawer, shelf or other receptacle in which medical items are stored. Typically, there are multiple storage containers in an inventory space.

The inventory sensors 24 include devices that sense the removal or addition of DMEPOS items from or to the inventory space. In one embodiment, the inventory sensors 24 include weight sensors attached to storage bins within the inventory space. In this embodiment, the inventory sensors 24 sense that one or more items have been added to a bin based on an increase in weight of the bin, and that one or more items have been removed from the bin based on a decrease in weight of the bin. With this system, particular bins are designated to hold particular items, so that a change in weight of the bin can be associated with a change in inventory of the corresponding item.

In some embodiments, the inventory sensors 24 include RFID sensors that sense the presence of RFID tags attached to DMEPOS items or other medical items within the inventory space. When an RFID tag on an item is within range of the RFID sensors, the tagged item is designated as being in inventory. Conversely, when the RFID tag on an item is outside the range of the RFID sensors, the tagged item is designated as being removed from inventory.

In another embodiment, the inventory sensors 24 include RFID sensors that sense the presence of RFID tags attached to DMEPOS items or other medical items when in range of the sensors. When an RFID tag on an item is within range of the RFID sensors, the tagged item is designated as being removed from inventory. Conversely, when the RFID tag on an item is outside the range of the RFID sensors, the tagged item is designated as being in inventory.

In some embodiments described herein, the inventory sensors 24 include RFID sensors that sense the presence of RFID tags attached to things other than medical items, such as RFID tags attached to personnel, patient charts or other physical documentation, or storage/transport bins.

In yet another embodiment, the inventory sensors 24 include one or more digital imaging devices, such as still cameras or video cameras, that capture images of items as the items are removed from or placed into the inventory space. In this embodiment, each item is marked with a distinctive identifier, such as a bar code, QR code, or other symbol, that uniquely identifies the item. The imaging devices are positioned such that their field of view will encompass an area through which items must pass as the items are removed from or added to the inventory space. Movement within the field of view triggers the imaging devices to capture multiple images of the items, such that at least one of the captured images may show the distinctive identifier on each item. Software executed on the customer computer 18, either as a module of the inventory client application 20 or a separate application, processes the image of the distinctive identifier (such as by "reading" a bar code or QR code) and provides identification information indicating which item is captured in the image.

In the embodiments discussed above, the inventory sensors 24 are substantially automatic. That is, they detect the addition and removal of items to and from inventory without human interaction. In a third embodiment, human interaction is required. In this embodiment, the inventory sensors 24 include barcode readers, and when a DMEPOS item is added to or removed from inventory, this is logged by scanning a barcode attached to the item.

The EMR computer system 26 comprises one or more computers that store and manage records regarding the status of patients receiving treatment in a medical facility. Generally, a patient's status is either admitted to the facility, discharged from the facility, or transferred to another department, location or facility.

In preferred embodiments, an inventory indicia device 27 is provided for each bin, shelf or drawer in the inventory space. These devices 27 preferably comprise an LED or LCD or other lighted display device disposed adjacent each bin, shelf or drawer. Depending on the current mode of operation, these devices 27 may provide a display of the number of items currently in each associated bin, shelf or drawer, or they may display a number of items that are to be added to the associated bin, shelf or drawer during a replenishment process as describe in more detail hereinafter. These indicia devices 27 are preferably controlled by the customer computer 18 based on the executed instructions of the inventory application 20.

The billing/claims computer system 28 comprises one or more computers that store and manage records regarding the billing for services rendered and DMEPOS items dispensed in examining, diagnosing, and treating patients. In preferred embodiments, this system 28 generates bills (in paper or electronic form) that are sent to patients, and generates claims that are sent to private insurers and Medicare/Medicaid. In some embodiments, the billing/claims computer system 28 is operable to communicate with a billing computer system 31 of a third-party DME supplier, such as through a secure Internet connection. As the term is used herein, a "third-party DME supplier" is any DME supplier other than the "Service Provider" which is the supplier entity that maintains the service provider computer network 14.

As the term is used herein, "billing codes" are standardized codes that have been assigned by standard-setting agencies to identify various medical services and devices for billing/reimbursement purposes. For example, Healthcare Common Procedure Coding System (HCPCS) Level II codes represent medical supplies, durable medical goods, non-physician services, ambulance services, and durable medical equipment, prosthetics, orthotics and supplies (DMEPOS). The HCPCS codes for orthotic/prosthetic devices are also referred to as "L-codes." HCPCS Level I codes are also referred to as Current Procedural Terminology (CPT) codes. Among other things, such billing codes indicate dollar amounts that are reimbursable under Medicare for medical examinations/treatments and for medical items prescribed for treatment.

As the term is used herein, "diagnostic codes" are standardized codes that have been assigned by standard-setting agencies for various medical diagnoses of diseases and injuries. For example, International Classification of Diseases (ICD) codes are used to classify diseases and other health problems recorded on many types of health and vital records, including death certificates and health records.

As the term is used herein, a "Super Bill" is an insurance claim document generated to request reimbursement from a payer entity to cover the cost of medical services and prescribed medical items that are provided to a patient. Generally, a Super Bill includes the name, credentials, office address and federal tax ID number of the medical service provider, the date(s) of the service provided, HCPCS codes for services provided and medical items prescribed, ICD codes for diagnoses, and the total fees charged for services and prescribed items.

With continued reference to FIG. 1, the service provider computer network 14 comprises one or more computers that store information and execute software for medical product/supply dispensing, billing and inventory management. As the term is used herein, a "Service Provider" may be a company that maintains inventories of DMEPOS items that are supplied to the customer to be dispensed to patients. An example of one such Service Provider is DeRoyal Industries, Inc. of Powell, Tennessee. Alternatively, the Service Provider may not maintain the inventory, but may provide inventory management services for another company that maintains the inventory.

In the embodiment of FIG. 1, the service provider computer network 14 includes an inventory management server computer 30 running an inventory server application 32, an electronic data interchange (EDI) server 34, and a product inventory database 36. The EDI server 34, which may be a J.D. Edwards/Oracle server, executes programs for implementing electronic commerce transactions between the service provider network 14 and the customer network 12. The product inventory database 36 stores records indicating quantities, coding, use and application of DMEPOS items in the Service Provider's inventory.

Figure 2:
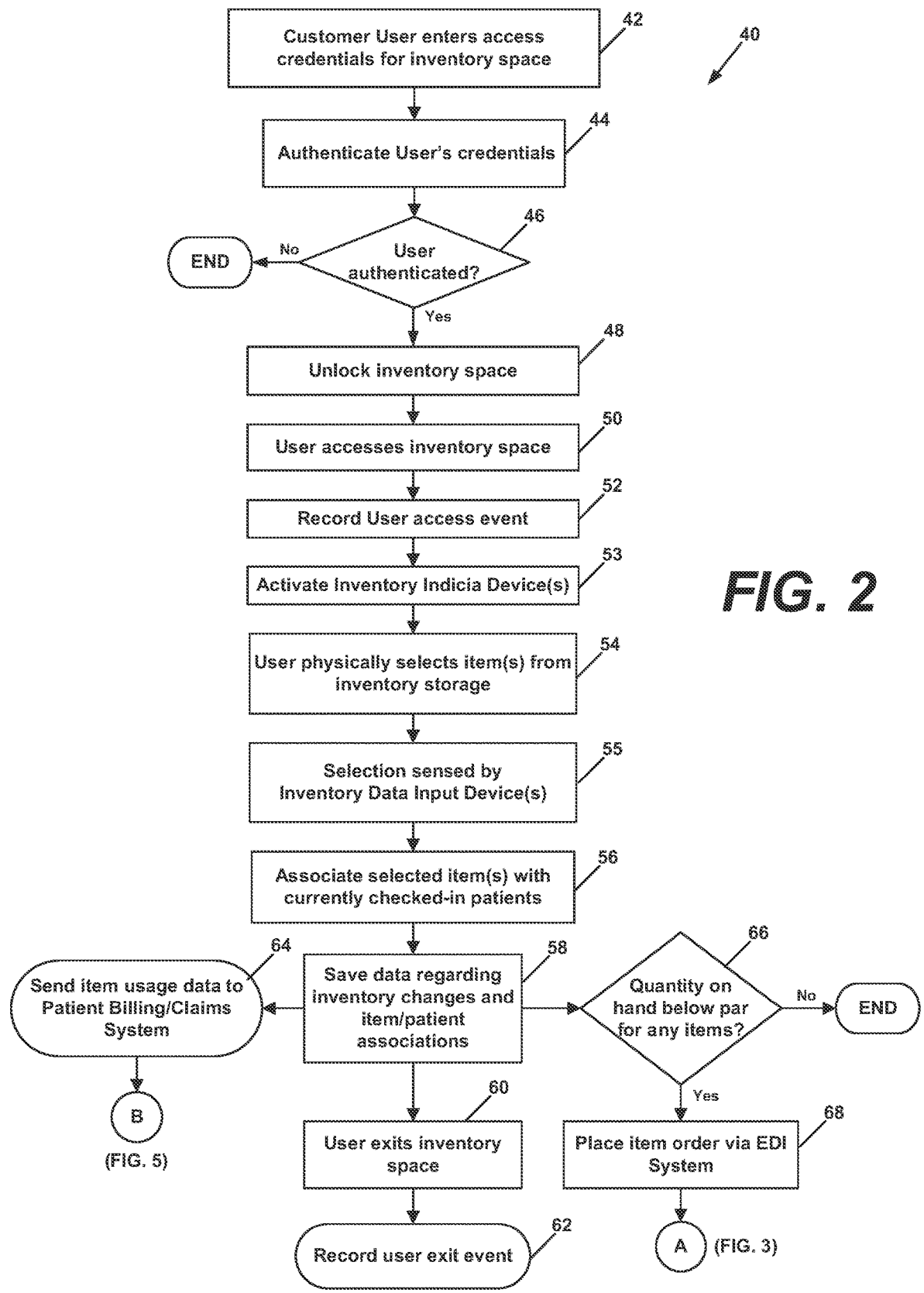
FIGS. 2 and 3 are flowcharts describing the operation of an embodiment of a medical product/supply dispensing, billing and inventory management system.

FIG. 2 depicts a process 40 for providing access to DMEPOS items in the inventory space of the customer facility, for logging removal of inventory items, and for billing the patient accordingly. Generally, the process 40 begins when a customer user enters credentials for gaining access to the inventory space (step 42). In one embodiment, this is accomplished by swiping a magnetic stripe on an ID card through a card reader of the inventory space access control system 22 (FIG. 1). In another embodiment, this is accomplished by swiping a proximity card near a proximity reader. In another embodiment, this involves reading an RFID tag with an RFID reader. In another embodiment, this involves entering a code on a keypad. In yet another embodiment, this involves a retina scan or a thumbprint scan using a biometric scanning device. In still another embodiment, this involves capturing an image of the user's face with a digital camera and processing the image using facial recognition software.

After entry of the customer user's credentials, the inventory client application 20 running on the customer computer 18 authenticates the credentials (step 44), such as by comparing the credentials to records saved in an authorized user database 29. The authorized user database 29 may be maintained on the customer network 12 or on the service provider network 14. In preferred embodiments, the system does not just check to verify that the user's access code is listed in the database 29. Rather, the system determines the identity of the user at the time of entry based on information stored in the database 29 and correlates the user identity information to inventory activities performed while the user has access to the inventory space.

If the user's credentials are not authenticated (step 46), the door of the inventory space remains locked and no further action is taken, other than to log a failed entry attempt. If the user's credentials are authenticated, the inventory client application 20 executes a command to unlock a door or other access port to the inventory space (step 48) and the user may access the space (step 50). The inventory client application 20 then updates a user entry log to record this user access event, with the date and time of access and the name/ID number of the user (step 52). Additionally, the user is logged into the application 20.

In some embodiments, the inventory indicia devices 27 are activated to display to the user the quantity of each item that is to be removed from each bin, shelf or drawer in the inventory space, and the number is automatically decremented as the items are removed (step 53).

When the user selects one or more items from the shelves, bins, or drawers of the inventory space (step 54), the selection is sensed by one or more of the inventory sensors 24 and corresponding selection data is provided to the inventory client application 20 (step 55). In a preferred embodiment, a list of the selected items is then displayed on the display screen 19 for viewing by the user. In situations wherein a bill of material (BOM) has been generated for refilling a procedural tray or other kit of items and the BOM has been accessed by the inventory client application 20, the sensors 24 sense whether the correct number of items have been removed from the shelves, bins or drawers as indicated by the BOM.

In one embodiment, the user uses the input device 21 to input information that the inventory client application 20 uses to associate each selected item with a currently admitted or checked-in patient in the facility (step 56). To input this information, the user may select the patient's name from a list displayed on the display device 19, which list is generated from data accessed from the EMR computer system 26. Alternatively, the user may scan a barcode assigned to the patient that is attached to the patient's chart/paperwork. In other embodiments, the patient is associated with the selected DMEPOS item by patient information included in RFID tag on the patient's chart/paperwork.

The inventory client application 20 saves data regarding the removal of items from inventory (also referred to as item usage data) and data indicating the item/patient association (step 58). The item usage data and item/patient association data are sent to the patient billing/claims computer system 28 for further processing (step 64). For example, the patient billing/claims computer system 28 may use this data to submit claims for payment to appropriate insurance providers.

Figure 5:
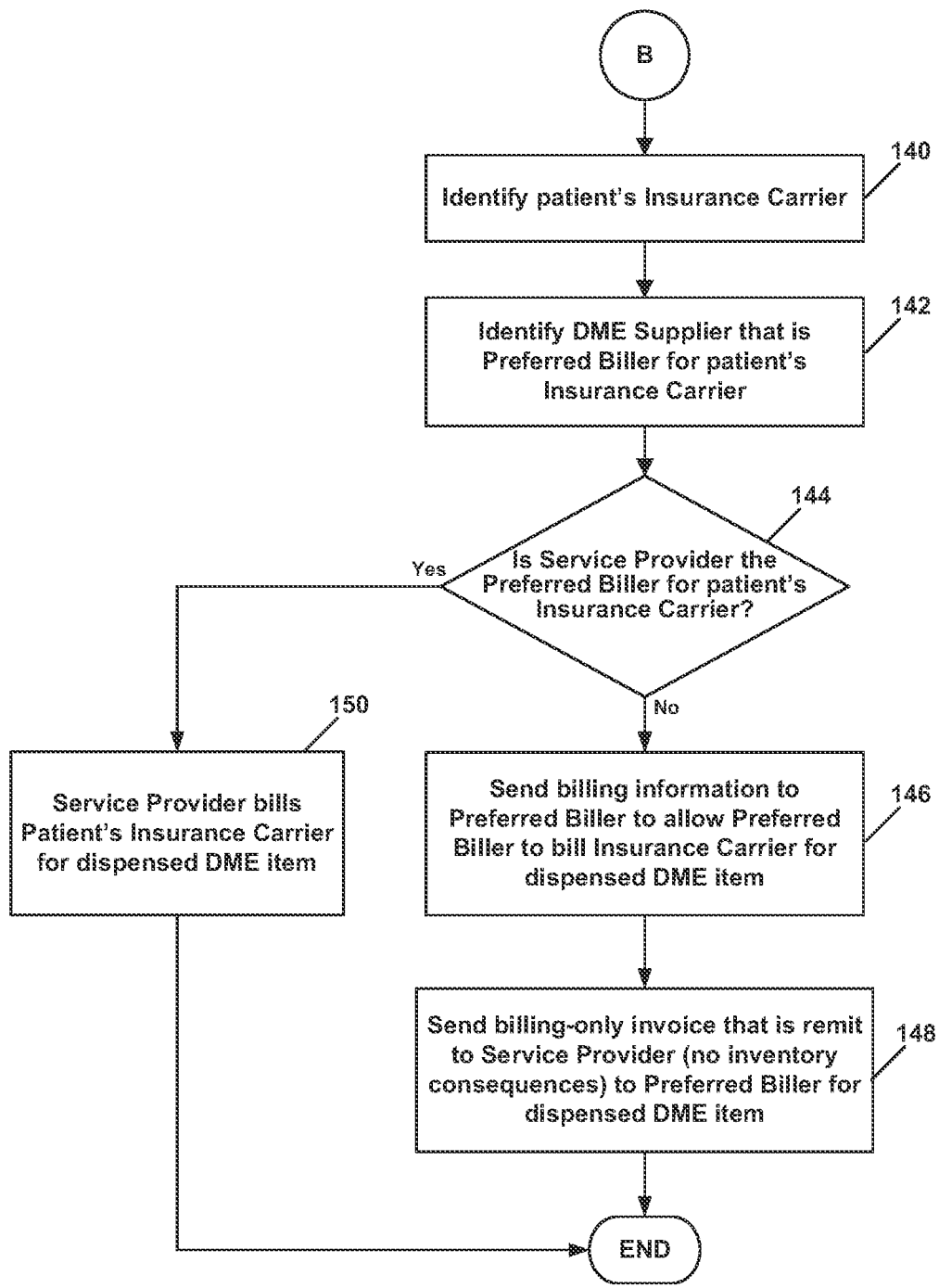
FIG. 5 depicts a flowchart describing the processing of billing information related to a dispensed DME item.

In one preferred embodiment, the patient billing/claims computer system 28 executes a billing process as depicted in FIG. 5. First, the patient's insurance carrier is identified (step 140). This determination may be made based on patient records stored in the EMR computer system 26 (FIG. 1). The system then identifies the DME supplier that is the preferred biller for the patient's insurance carrier (step 142). Table I provides an example listing of insurance carriers in association with their preferred biller DME suppliers. For example, DeRoyal Continuum is the DME supplier that is the preferred biller for Blue Cross Blue Shield. Information associating insurance carriers and preferred billers may be stored in a database connected to the customer network 12 or the service provider network 14 or both.

TABLE I

| Insurance Carrier | DME Supplier |
|---|---|
| Blue Cross Blue Shield | DeRoyal Continuum |
| Humana | Bob Jones Medical Supply |
| Medicare | Lambert's Health Care |
| Other insurance carrier | Other DME supplier |

As shown in FIG. 5, if the Service Provider is the DME supplier that is the preferred biller for the patient's insurance carrier (step 144), the Service Provider bills the insurance carrier for the dispensed DME item (step 150). If the Service Provider is not the preferred biller for the patient's insurance carrier (step 144), billing information for the dispensed item is sent to the preferred biller so the preferred biller can bill the patient's insurance carrier (step 146). The billing information may be on a one-page document that provides the patient demographics, insurance carrier information and dispensed DME. A billing-only invoice that is remit to the Service Provider (no inventory consequences) is also sent to the preferred biller for the dispensed DME item (step 148).

Consider the following example. DeRoyal Continuum is the Service Provider for Tennova Healthcare. A low-profile walker is dispensed to John Smith, a patient of Tennova. Blue Cross Blue Shield is John Smith's insurance carrier. Since DeRoyal Continuum is the preferred biller for Blue Cross Blue Shield, DeRoyal Continuum submits a bill to Blue Cross Blue Shield for the low-profile walker.

Now consider an example in which a knee brace is dispensed to Susan White, also a patient of Tennova. Susan's insurance carrier is Humana, and Bob Jones Medical Supply is the preferred biller for Humana. In this situation, since DeRoyal Continuum is the Service Provider, but not the preferred biller, all billing information is sent to Bob Jones Medical Supply so that Bob Jones can bill Humana for the knee brace. A billing-only invoice is also sent to Bob Jones and is remitted to DeRoyal Continuum for the knee brace.

With reference again to FIG. 2, based on the item usage data, the inventory client application 20 determines whether the remaining quantity of inventory items is below a predetermined minimum threshold (step 66). If so, the inventory client application 20 places an order for some quantity of the items via the Internet connection to the Service Provider's EDI server 34 (step 68). Alternatively, the inventory client application 20 sends an email or other electronic message to the person responsible for maintaining the inventory to remind the person to place an order.

After the user has associated the items taken from inventory with one or more patients (step 56), the user may exit the inventory space (step 60) and the inventory client application 20 logs a user exit event (step 62). In some embodiments wherein the inventory space is a room or cage, the inventory room door may not be opened to allow the user to exit until the user has done whatever is needed to complete item/patient association (step 56). In other embodiments, the door may be opened, but if the item/patient association has not been completed beforehand, an alarm sounds to remind the user to complete that task before leaving. In some embodiments, if the user leaves the inventory space without completing the item/patient association, the user will receive an email or text message reminding the user to complete the task.

By logging access and exit events for specific users, the system 10 keeps track of each user that accesses the inventory space, and it associates the items removed from or added to inventory with the dates/times that each user accessed the inventory space. This provides for user accountability in the inventory process.

Figure 3:
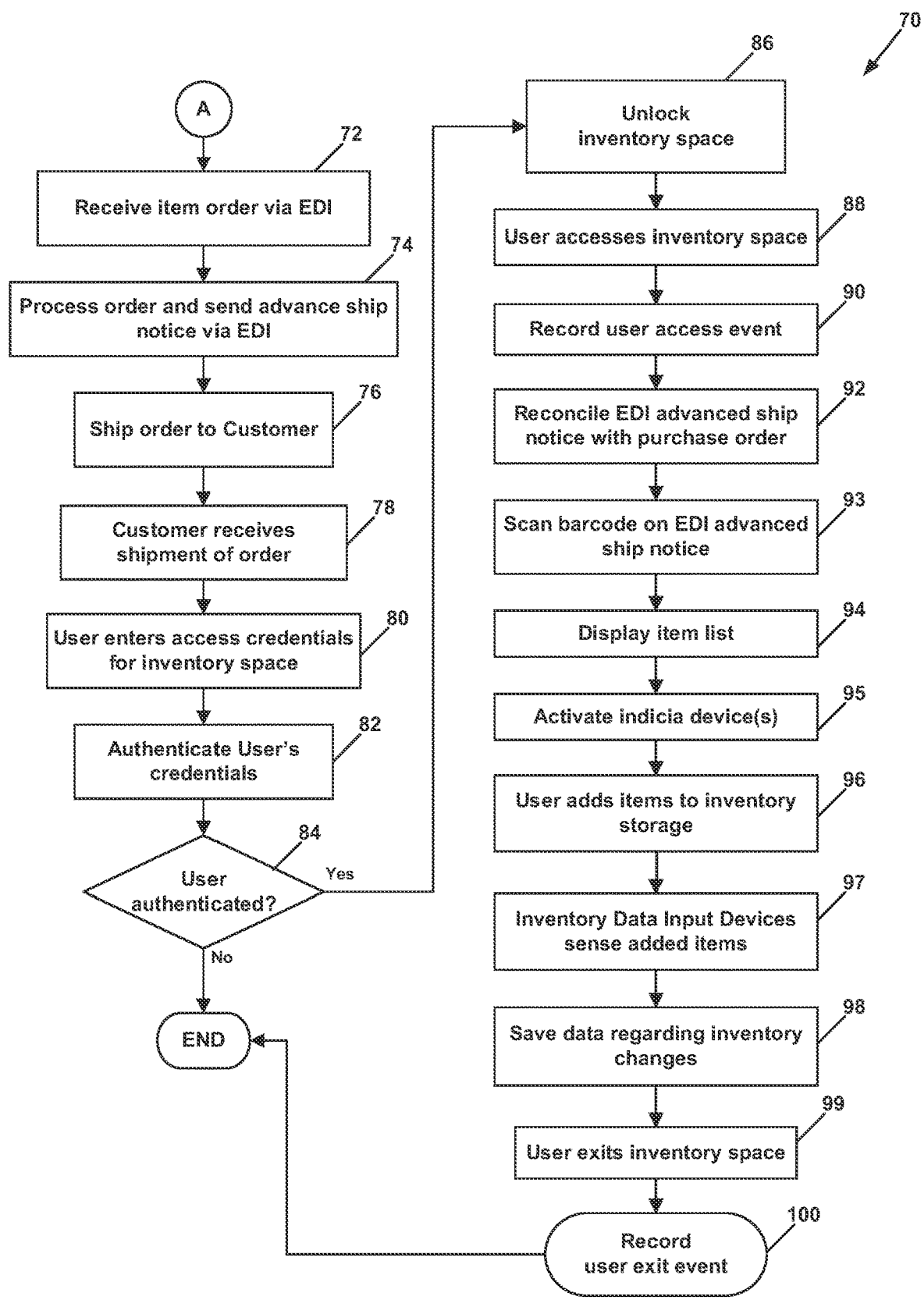

FIG. 3 depicts a preferred embodiment of a process 70 for replenishing items in the inventory space of the customer facility. Initially, the Service Provider's inventory server application 32 receives the order for items (step 72) that was placed by the inventory client application 20 in step 68 of FIG. 2. The inventory server application 32 passes the order to the EDI server 34. The EDI server 34 processes the order and sends an advance ship notice to the customer via the inventory server application 32 (step 74). The Service Provider then ships the ordered items (step 76) and the customer receives the ordered items (step 78). The customer user then takes the received items to the inventory space to restock the inventory. The customer user enters credentials for gaining access to the inventory space (step 80), such as by swiping a magnetic stripe on an ID card through a card reader of the inventory space access control system 22. The inventory client application 20 running on the customer computer 18 authenticates the user's credentials (step 82) as described above.

If the user's credentials are not authenticated (step 84), the door or entry port of the inventory space remains locked and no further action is taken, other than to log a failed entry attempt. If the user's credentials are authenticated, the inventory client application 20 executes a command to unlock the inventory space door or entry port (step 86) and the user may access the inventory space (step 88). The inventory client application 20 then updates a user entry log to record this user access event, with the date and time of access and the name/ID number of the user (step 90). Alternatively or in addition, the inventory server application 32 may update a user access log maintained on the service provider server 30.

The user reconciles the EDI advance ship notice with the purchase order that was issued in step 68 of FIG. 2 (step 92). In a preferred embodiment, this process includes scanning a barcode or other unique identifier on the EDI advance ship notice (step 93), at which point the inventory client application 20 accesses item replenishment information, such as a list of items associated with the identified EDI advance ship notice, and displays this information on the display device 19 (step 94). Based on the item replenishment information, the application 20 also activates the appropriate inventory indicia devices 27 associated with each bin, shelf, or drawer in the inventory space to indicate which bins, shelves or drawers are to receive replenishment items, and how many items are to be put in each bin, shelf or drawer (step 95). This activation may comprise turning on or lighting up indicia devices 27 that were previously in an off condition, or causing the indicia devices 27 to flash in some manner to attract the user's attention.

When the user physically adds the replenishment items to the appropriate bins, shelves, or drawers in the inventory space (step 96), the addition is automatically sensed by one or more of the inventory sensors 24 (such as by sensing additional weight in a bin or by sensing the presence of previously unlogged RFID tags on the added items) and the corresponding replenishment data is provided to the inventory client application 20 (step 97). The inventory client application 20 records the data indicating an addition of items to inventory (step 98). In a preferred embodiment, a list of the added items is displayed on the display screen 19 for viewing, confirmation, and editing by the user. When the user exits the inventory space (step 99), the inventory client application 20 logs a user exit event (step 100).

Figure 6:
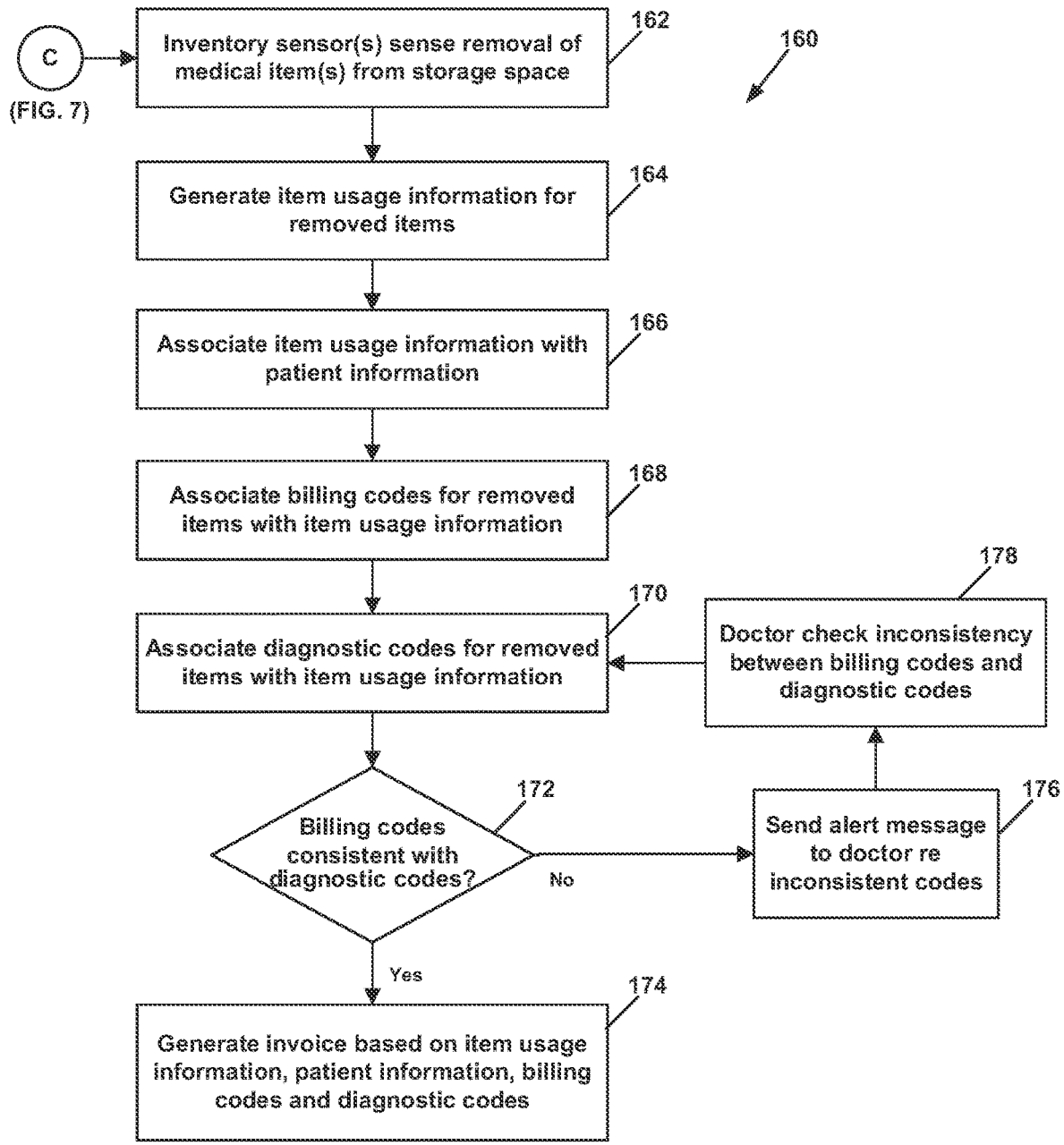
FIGS. 6, 7 and 8 are flowcharts describing further operations of an embodiment of a medical product/supply dispensing, billing and inventory management system.

In another preferred embodiment, the customer computer 18 executes a billing process 160 as depicted in FIG. 6. As described in previous embodiments, inventory sensors 24 in the inventory storage space detect that one or more medical items have been removed from a storage container to be used in a medical procedure or otherwise dispensed for treatment of a patient (step 162). Triggered by this removal, the customer computer 18 generates item usage data identifying the items removed and the quantity of each (step 164), and the item usage data is associated with patient data that identifies the patient to which the medical items are to be dispensed (step 166). The customer computer 18 also associates the billing codes (such as HCPCS codes) for the removed items with the item usage data and the patient data (step 168). In some preferred embodiments, one or more diagnostic codes (such as ICD codes) that have been entered by the treating physician are also associated with the billing codes, the item usage data and the patient data for the removed items (step 170). The customer computer 18 preferably accesses the product database 36 and verifies that each billing code identifies an item that is appropriate for treatment of the injury or condition indicated by a diagnostic code (step 172). If a billing code is not consistent with a diagnostic code, an alert message (such as an email) is automatically generated and sent to the doctor responsible for treatment of the patient (step 176). This prompts the doctor to check on the inconsistency and take action to resolve the matter (step 178). If the billing and diagnostic codes are consistent (step 172), the customer computer 18 or the patient billing/claims system 28 generates an invoice (also referred to as a Super Bill) to be sent to the patient's insurance provider for reimbursement (step 174). This invoice preferably includes the item usage information, patient information, billing codes and diagnostic codes.

As shown in FIG. 1, some embodiments of the invention include a physician interface computer 15, which may be a personal computer, laptop computer, tablet/pad computer, smart phone, or other such computing device. During an examination of a patient, a physician may use the physician interface computer 15 to access and follow diagnostic/treatment protocol guidelines, record diagnostic information, record patient information, make notes, and order DMEPOS items to be dispensed to the patient as part of the patient's treatment. Preferably, the physician interface computer 15 is operable to communicate with the customer network 12 and the service provider network 14 via the Internet 16 or other communication network. In a preferred embodiment, a physician may use the physician interface computer 15 to prescribe DMEPOS items in inventory that a patient needs, and send the order data for the prescribed items to the inventory client application 20 running on the customer computer 18.

Figure 7:
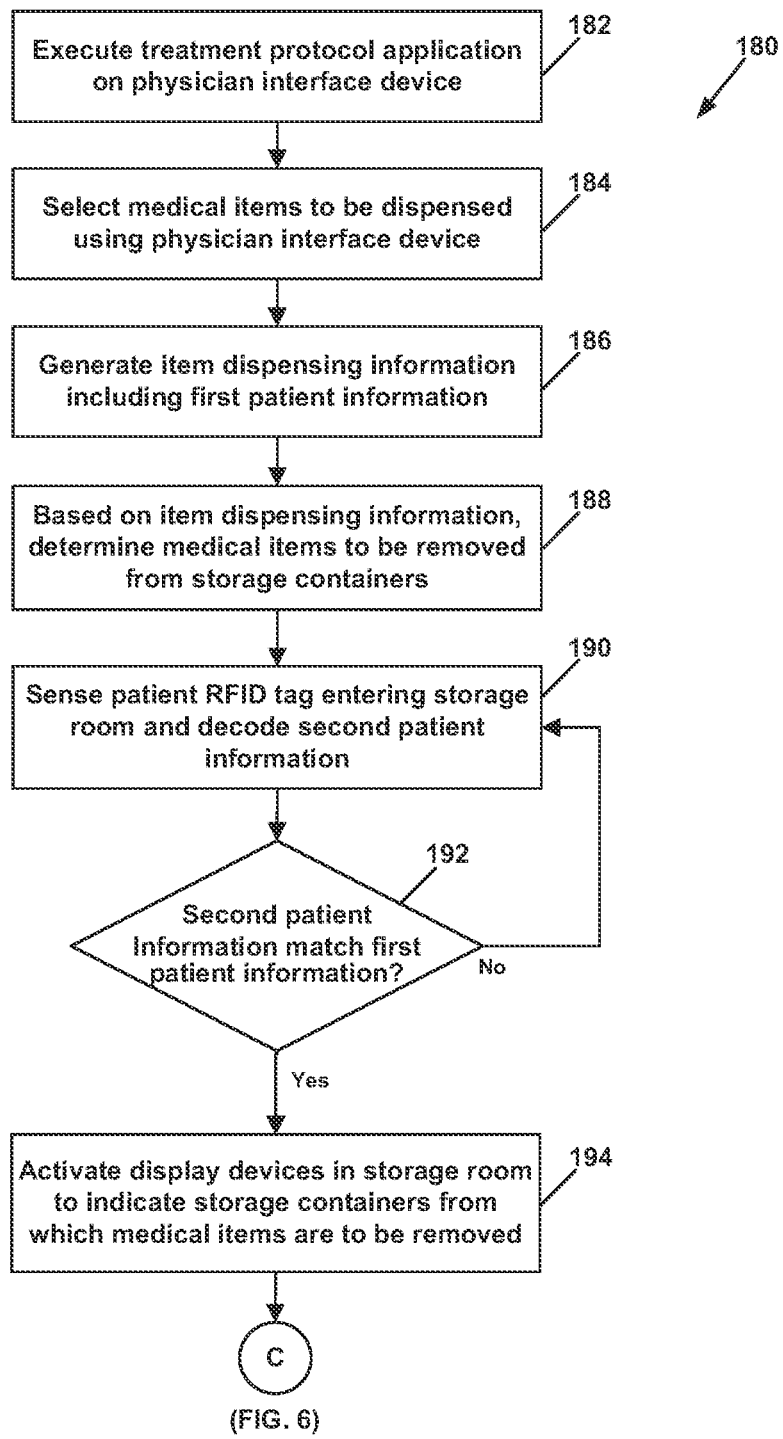

As alluded to above, the physician interface computer 15 may be used to access diagnostic/treatment protocol guidelines for various types of injuries, such as orthopedic injuries. Preferably, these guidelines are provided in a web-based application that may be accessed via the Internet 16 using the physician interface computer 15. In one preferred embodiment depicted in FIGS. 1 and 7, the guidelines are provided by a treatment protocol application 33 that is executed on the service provider server 30 (step 182). The guidelines may include checklists and tips for diagnosis, treatment, documentation, and billing for various types of injuries. Preferably, the guidelines include a list of related medical items, such as DMEPOS items, that can be dispensed for treatment of a diagnosed condition. These items can be ordered via the service provider network 14 and the EDI server 34 or they may be dispensed directly from a supply room at the medical facility as described hereinafter.

In some embodiments, the treatment protocol application 33 displays listings on the physician interface computer 15 of reimbursement billing codes (such as HCPCS codes) and diagnostic codes (such as ICD codes) associated with the types of injuries covered by the guidelines. As discussed above, the billing codes indicate Medicare-reimbursable amounts for the examination and for the medical items prescribed for treatment, and the diagnostic codes identify the type of injury or condition.

In some embodiments, the treatment protocol application 33 also displays listings of medical items that may be ordered from the Service Provider for treatment of the particular diagnosed injury, with links for directly ordering the items using the physician interface computer 15 (step 184). For example, for an orthopedic ankle injury, the treatment protocol application 33 may display a listing of available ankle braces, ankle stirrups and walking boots. The items are preferably listed in groups according the HCPCS code.

In addition to ordering medical items from the Service Provider for replenishing inventory, preferred embodiments of the treatment protocol application 33 allow the physician to use the physician interface computer 15 to dispense items from inventory at the doctor's office or clinic. In this embodiment, the treatment protocol application 33 generates and sends item dispensing information, which may include product codes and quantities for the items to be dispensed, a patient identifier, and a billing code to the inventory client application 20 (step 186). Based on the item dispensing information, the inventory client application 20 displays information on the display device 19 indicating the item to be dispensed, the bin, shelf or drawer where the item may be found in the inventory space, and patient identification information (step 188). Preferably, the inventory client application 20 activates the appropriate inventory indicia device 27 to indicate the bin, shelf or drawer where the item is located in the inventory space (step 194).

In a preferred embodiment, the inventory sensors 24 (FIG. 1) disposed in the inventory space include an RFID sensor 24 positioned to read patient identifier RFID tags that are attached to patient charts or to other patient documentation that enter the inventory space. When personnel enter the inventory space carrying a patient's chart/documentation to which a patient identifier RFID tag is attached, the RFID sensor 24 reads the patient identifier RFID tag and decodes patient identification information encoded in the patient identifier RFID tag (step 190 in FIG. 7). The customer computer 18 then determines whether the patient identification information encoded in the patient identifier RFID tag matches patient identification information included in the item dispensing information (see step 186) that was generated by the treatment protocol application 33 (step 192). If there is a match, the customer computer 18 activates one or more display devices in the inventory space to direct the personnel to the appropriate supply bin from which to pull the medical item that was prescribed by the doctor for treatment of the patient (step 194). In one embodiment, this involves displaying the information on the display device 19 in the inventory space. In another embodiment, this involves activating one or more inventory indicia devices 24 in the inventory space, such as turning on or flashing a light on the appropriate supply bin, or displaying a number on an alphanumeric display device on the supply bin indicating the quantity of items to be pulled from the bin.

In some embodiments, when the physician uses the treatment protocol application 33 to dispense a particular medical item for a patient, the treatment protocol application 33 verifies that the HCPCS code identifies an item that is reimbursable and appropriate for treatment of the injury or condition indicated by the diagnostic code entered in the patient's record. If the item is not appropriate, the treatment protocol application 33 displays a message prompting the physician to double check that the correct item is being dispensed for treatment of the particular injury or condition.

Although some embodiments of the invention are directed to dispensing, billing and inventory management for DME- POS items, the apparatus and methods described herein are also applicable to dispensing, billing and inventory management of other types of medical items, such as surgical implant items and items used in a catheter lab. Thus, "medical item" as that term is used herein is not limited to DMEPOS items or any other particular type of medical item.

Figure 8:
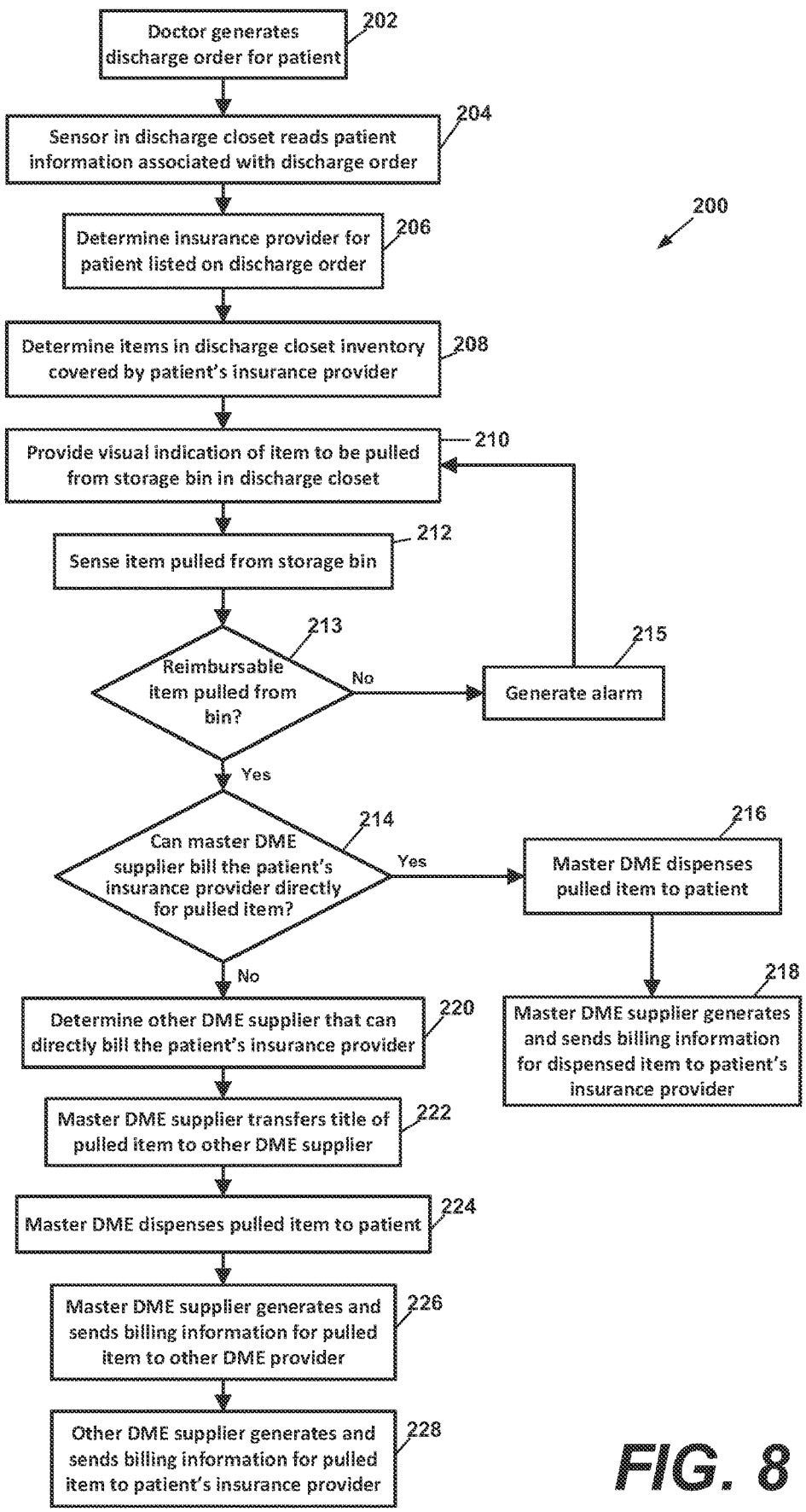

In another preferred embodiment, the customer computer 18 executes a dispensing and billing process 200 as depicted in FIG. 8 for items dispensed to a patient after discharge. Such items may be dispensed from a supply room in which post-discharge medical items are stocked, which is also referred to herein as a discharge closet. In a preferred embodiment, a single DME supplier (such as Pinnacle Medsource) has a contract with the medical facility to provide all of the inventory in the discharge closet. This supplier, also referred to herein as the master DME supplier, owns all of the items in the discharge closet until ownership of an item is transferred to the patient or to an intermediary DME supplier as described in more detail hereinafter.

With reference to FIGS. 1 and 8, prior to discharge of a patient, the doctor uses the physician interface computer 15 or another networked computer to generate a discharge order for the patient (step 202). The discharge order includes a listing of medical items that are to be dispensed to the patient after discharge for the patient's use at home. For example, the discharge order may call for a knee brace or other DMEPOS item.

In a preferred embodiment, one or more RFID sensors 24 are disposed in the discharge closet and are positioned to read patient identifier RFID tags that are attached to a discharge order or to other patient documentation that enters the space. When a person enters the discharge closet carrying a patient's discharge order to which a patient identifier RFID tag is attached, the RFID sensor 24 reads the patient identifier RFID tag and decodes the patient identification information encoded in the patient identifier RFID tag (step 204). Based on the patient identification information, the customer computer 18 accesses the database 36 to determine the patient's insurance provider (step 206). The customer computer 18 also accesses the inventory of items in the discharge closet from the database 36 and determines which items are covered by the patient's insurance provider (step 208). For example, the discharge closet may contain knee braces from three different manufacturers that meet the requirements of the item prescribed by the doctor as identified on the discharge order. However, the patient's insurance may reimburse for a knee brace from only one of the manufacturers.

In a preferred embodiment, the customer computer 18 activates one or more display devices in the discharge closet to direct the personnel to the appropriate supply bin from which to pull the reimbursable version of the medical item listed on the discharge order (step 210). In one embodiment, this involves displaying the information on a display device 19 in the discharge closet. In another embodiment, this involves activating one or more inventory indicia devices 24 in the discharge closet, such as turning on or flashing a light on the appropriate supply bin, or displaying a number on an alphanumeric display device on the supply bin indicating the quantity of items to be pulled from the bin. The person then pulls the item from the storage bin indicated by the display device 19 or the indicia device 24 (step 212).

Inventory sensors 24 in the discharge closet, such as RFID sensors or weight sensors, detect when the pulled item is removed from the storage bin or removed from the discharge closet (step 214). Triggered by this removal, the customer computer 18 determines whether the item pulled from the bin is in fact reimbursable by the patient's insurance provider (step 213). This check is performed to detect situations such as when an item was pulled from the wrong bin, or an item is pulled from the correct bin but it is the wrong item. If the wrong item was pulled, a visual or audible alarm is generated in the discharge closet and a message is displayed on the display device 19 indicating the mistake (step 215), and an indicia device 24 is again activated indicating the correct supply bin (step 210).

If the correct item has been pulled from the bin, the customer computer 18 accesses the database 36 to determine whether the pulled item is one for which the master DME supplier can directly bill the patient's insurance provider (step 214). If the master DME supplier can seek reimbursement directly from the patient's insurance provider, the pulled item is dispensed to the patient (step 216), and the customer computer 18 generates the appropriate documentation indicating that ownership of the item has passed from the master DME supplier to the patient. The customer computer 18 also generates billing information to be sent to the patient's insurance provider for reimbursement to be paid to the master DME supplier.

If the pulled item is not one for which the master DME supplier can directly bill the patient's insurance provider (step 214), the customer computer 18 accesses the database 36 to determine which other DME supplier can seek reimbursement directly from the patient's insurance provider (step 220). Based on the identity of the other DME supplier determined in step 220 (also referred to herein as the intermediary DME supplier), the customer computer 18 generates the appropriate documentation to effect a transfer of ownership of the item from the master DME supplier to the intermediary DME supplier (step 222). After this first transfer of ownership, the master DME supplier dispenses the pulled item to the patient, and the customer computer 18 generates the appropriate documentation effecting a second transfer of ownership from the intermediary DME supplier to the patient (step 224). In preferred embodiments, the customer computer 18 also generates billing information to be sent to the intermediary DME supplier requesting reimbursement to be paid to the master DME supplier (step 226). The intermediary DME supplier may then generate billing information to be sent to the patient's insurance provider for reimbursement to be paid to the intermediary DME supplier (step 228).

It should be appreciated that many of the process steps listed in FIGS. 2, 3, and 5-8 may be performed by the inventory server application 32, by the inventory client application 20, or by both working together. Thus, the invention is not limited to performance of the process steps by any particular application or on any particular computer system.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An inventory management system for managing information regarding medical items listed on a discharge order to be dispensed in conjunction with medical treatment of a patient, wherein the medical items are disposed in storage containers in a discharge closet, the inventory management system comprising:
one or more RFID sensors disposed in the discharge closet, the one or more RFID sensors operable to sense patient identification information encoded in an RFID tag attached to the discharge order as or after the discharge order enters the discharge closet;
one or more display devices disposed in the discharge closet;
one or more computers in communication with the one or more RFID sensors and the one or more display devices, the one or more computers configured to store and process billing information for medical items dispensed to patients, the billing information including:
information that associates each patient with a medical insurance provider to which medical expenses incurred by the patent are to be billed; and
information that associates medical items stored in the discharge closet with medical insurance providers that provide reimbursement for the associated medical items; and
one or more software applications executed on the one or more computers, the one or more software applications including computer-executable instructions that:
process the patient identification information to identify a patient associated with the discharge order;
process the billing information to identify a medical insurance provider to which medical expenses incurred by the patient associated with the discharge order are to be billed;
process the billing information to identify medical items stored in the discharge closet for which reimbursement is provided by the identified medical insurance provider; and
activate the one or more display devices in the discharge closet to visually indicate one or more of the storage containers in which the identified medical items are disposed,
wherein the one or more computers execute all of the computer-executable instructions automatically based on the one or more RFID sensors sensing the patient identification information encoded in the RFID tag attached to the discharge order as or after the discharge order enters the discharge closet.

2. The inventory management system of claim 1 further comprising:
one or more inventory sensors for sensing removal of a medical item from one of the storage containers, the one or more inventory sensors including one or more of:
a weight sensor attached to the storage container from which the medical item was removed;
an RFID sensor for sensing the presence of an RFID tag attached to the removed medical item;
a bar code reader for scanning a barcode on the removed medical item; and
a digital camera for capturing an image of the removed medical item; and
the one or more software applications including computer-executable instructions that:
identify the removed medical item based on a signal from the weight sensor attached to the storage container from which the medical item was removed, or based on information contained in the RFID tag attached to the removed medical item, or based on information contained in the barcode on the removed medical item, or based on the image of the removed medical item;
determine whether the removed medical item is a medical item for which reimbursement is provided by the identified medical insurance provider; and
generate an alarm based on determining that the removed medical item is not a medical item for which reimbursement is provided by the identified medical insurance provider.

3. The system of claim 2 wherein the one or more software applications include computer-executable instructions that are automatically executed based on the removal of the medical item as sensed by the one or more inventory sensors, which instructions generate user information that identifies personnel responsible for removal of the medical item from the discharge closet.

4. The inventory management system of claim 2 wherein the one or more software applications include computer-executable instructions that:
process the billing information to determine whether a master DME supplier can bill the identified medical insurance provider directly for the removed medical item; and
generate a bill from the master DME supplier directed to the identified medical insurance provider for reimbursement for the removed medical item, based on determining that the master DME supplier can bill the identified medical insurance provider directly for the removed medical item.

5. The inventory management system of claim 4 wherein the one or more software applications including computer-executable instructions that:
process the billing information to identify an alternative DME supplier that can bill the identified medical insurance provider directly for the removed medical item, if it is determined that the master DME supplier cannot bill the identified medical insurance provider directly for the removed medical item;
generate a bill from the master DME supplier directed to the identified alternative DME supplier for reimbursement for the removed medical item; and
generate a bill from the identified alternative DME supplier directed to the identified medical insurance provider for reimbursement for the removed medical item.

6. The inventory management system of claim 1 wherein the one or more display devices comprise a plurality of lights disposed in the discharge closet, each light associated with a corresponding one of the storage containers, wherein each light is operable to provide a visual indication that one or more medical items are to be removed from the storage container associated with the light.

7. The inventory management system of claim 1 wherein the one or more display devices comprise a display screen operable to display information listing one or more medical items that are to be removed from the storage containers to be dispensed to the patient as indicated by the discharge order.

8. The system of claim 1 wherein the storage containers comprise bins, shelves, or drawers within the discharge closet.

9. An inventory management system for managing information regarding medical items listed on a discharge order to be dispensed in conjunction with medical treatment of a patient, wherein the medical items are disposed in storage containers in a discharge closet, the inventory management system comprising:

one or more RFID sensors disposed in the discharge closet, the one or more RFID sensors operable to sense patient identification information encoded in an RFID tag attached to the discharge order as or after the discharge order enters the discharge closet;

one or more display devices disposed in the discharge closet;

one or more inventory sensors for sensing removal of a medical item from one of the storage containers, the one or more inventory sensors including one or more of:
      a weight sensor attached to the storage container from which the medical item was removed;
      an RFID sensor for sensing the presence of an RFID tag attached to the removed medical item;
      a bar code reader for scanning a barcode on the removed medical item; and
      a digital camera for capturing an image of the removed medical item; and one or more computers in communication with the one or more RFID sensors, the one or more display devices, and the one or more inventory sensors, the one or more computers configured to store and process billing information for medical items dispensed to patients, the billing information including:
      information that associates each patient with a medical insurance provider to which medical expenses incurred by the patent are to be billed; and
      information that associates medical items stored in the discharge closet with medical insurance providers that provide reimbursement for the associated medical items; and one or more software applications executed on the one or more computers, the one or more software applications including computer-executable instructions that:
      process the patient identification information to identify a patient associated with the discharge order;
      process the billing information to identify a medical insurance provider to which medical expenses incurred by the patient associated with the discharge order are to be billed;
      process the billing information to identify medical items stored in the discharge closet for which reimbursement is provided by the identified medical insurance provider;
      cause the one or more display devices to visually indicate one or more storage containers in which the identified medical items are disposed;
      identify the removed medical item based on a signal from the weight sensor attached to the storage container from which the medical item was removed, or based on information contained in the RFID tag attached to the removed medical item, or based on information contained in the barcode on the removed medical item, or based on the image of the removed medical item;
      determine whether the removed medical item is a medical item for which reimbursement is provided by the identified medical insurance provider;
      generate an alarm based on determining that the removed medical item is not a medical item for which reimbursement is provided by the identified medical insurance provider;
      process the billing information to determine whether a master DME supplier can bill the identified medical insurance provider directly for the removed medical item; and
      generate a bill from the master DME supplier directed to the identified medical insurance provider for reimbursement for the removed medical item, based on determining that the master DME supplier can bill the identified medical insurance provider directly for the removed medical item.

10. The inventory management system of claim 9 wherein the one or more computers execute the computer-executable instructions automatically based on the one or more RFID sensors sensing the patient identification information encoded in the RFID tag attached to the discharge order as or after the discharge order enters the discharge closet.

11. The system of claim 9 wherein the one or more software applications include computer-executable instructions that are automatically executed based on the removal of the medical item as sensed by the one or more inventory sensors, which instructions generate user information that identifies personnel responsible for removal of the medical item from the discharge closet.

12. The inventory management system of claim 9 wherein the one or more software applications including computer-executable instructions that:
   process the billing information to identify an alternative DME supplier that can bill the identified medical insurance provider directly for the removed medical item, if it is determined that the master DME supplier cannot bill the identified medical insurance provider directly for the removed medical item;
   generate a bill from the master DME supplier directed to the identified alternative DME supplier for reimbursement for the removed medical item; and
   generate a bill from the identified alternative DME supplier directed to the identified medical insurance provider for reimbursement for the removed medical item.

13. The inventory management system of claim 9 wherein the one or more display devices comprise a plurality of lights disposed in the discharge closet, each light associated with a corresponding one of the storage containers, wherein each light is operable to provide a visual indication that one or more medical items are to be removed from the storage container associated with the light.

14. The inventory management system of claim 9 wherein the one or more display devices comprise a display screen operable to display information listing one or more medical items that are to be removed from the storage containers to be dispensed to the patient as indicated by the discharge order.

15. The system of claim 9 wherein the storage containers comprise bins, shelves, or drawers within the discharge closet.

* * * * *